United States Patent [19]

Böhmer

[11] Patent Number: 4,702,598
[45] Date of Patent: Oct. 27, 1987

[54] FLOW CYTOMETER

[75] Inventor: Ralph M. Böhmer, St. Kilda, Australia

[73] Assignee: Research Corporation, N.Y.

[21] Appl. No.: 704,800

[22] Filed: Feb. 25, 1985

[51] Int. Cl.$^4$ ............................................. G01N 21/47
[52] U.S. Cl. ......................................... 356/343; 356/73
[58] Field of Search ............................ 356/73, 335–338, 356/340, 343, 318; 250/574–575, 461.2, 227

[56] References Cited

U.S. PATENT DOCUMENTS

| | | | |
|---|---|---|---|
| 3,624,835 | 11/1971 | Wyatt | 250/220 X |
| 3,770,351 | 11/1973 | Wyatt | 356/338 |
| 3,869,208 | 3/1975 | Lorenz | 250/227 X |
| 3,869,209 | 3/1975 | Sigrist | 250/574 X |
| 3,880,523 | 4/1975 | Thomas | 356/411 X |
| 3,910,701 | 10/1975 | Henderson et al. | 356/39 |
| 3,910,702 | 10/1975 | Coril | 356/72 |
| 3,924,951 | 12/1975 | Dittrich | 356/335 |
| 3,992,101 | 11/1976 | Dapper et al. | 250/578 X |
| 3,992,631 | 11/1976 | Harte | 250/365 |
| 4,012,114 | 3/1977 | Eigenmann | 404/14 |
| 4,173,415 | 11/1979 | Wyatt | 356/336 |
| 4,188,121 | 2/1980 | Hirleman et al. | 356/343 |
| 4,222,064 | 9/1980 | Lodzinski | 356/73 |
| 4,281,924 | 8/1981 | Auer et al. | 356/73 |
| 4,318,180 | 3/1982 | Lundqvist et al. | 356/442 X |
| 4,412,742 | 11/1983 | Lloyd | 356/73 |
| 4,479,058 | 10/1984 | Gast et al. | 250/343 |
| 4,505,583 | 3/1985 | Konomi | 356/73 |
| 4,523,841 | 6/1985 | Brunsting et al. | 356/73 |
| 4,540,280 | 9/1985 | Anderson et al. | 356/246 |
| 4,541,719 | 9/1985 | Wyatt | 356/343 |

FOREIGN PATENT DOCUMENTS 739376 6/1980 U.S.S.R. .

OTHER PUBLICATIONS

Ratzlaff et al., Absorption-Corrected Fiber Optic Fluorometer, Anal. Chem., 1984, 56, 342–347.
Smith et al., Design and Evaluation of a Fiber Optic Fluorometric Flow Cell, Anal. Chem., vol. 49, No. 13, 1977.
Eisenlauer et al., Fibre-Optic Sensor Technique for Flocculant Dose Control in Flowing Suspensions, Colloids and Surfaces, 14 (1985), 121–134.
Nishiya et al., Proc. Japan Acad, 56, Ser. B (1980).

Primary Examiner—R. A. Rosenberger
Attorney, Agent, or Firm—Scully, Scott, Murphy & Presser

[57] ABSTRACT

A flow cytometer and a method for determining properties of single cells or other particles including passing stream of particles through a zone of analysis where a light source directs a beam of light to perpendicularly intersect the stream of particles so that only a single cell is exposed to the light beam. An array of optical fibres adjacent the zone of analysis collects the light refracted by the cells as each cell passes through the zone of analysis. Each fibre is connected to a photomultiplier for converting the light to electrical signals which are analyzed by an electronic analysis unit to determine the particle properties. The angle at which the light is collected by said optical fibre is adjustable to permit more light to be collected to yield more information about the particle.

6 Claims, 6 Drawing Figures

FLOW CYTOMETER

BACKGROUND OF THE INVENTION

The present invention relates to flow cytometers.

Flow cytometers (FCM) are instruments by which properties of single cells or other particles in suspension can be determined. Conventionally, an FCM consists of the following basic components:

i. A liquid flow system by which cells in suspension, which may be loaded with fluorescent dye, are transported in a vertical particle stream and passed singly, one after another, across a zone of analysis where they are exposed to an intense light beam. This zone may be located in open air or in a glass flow chamber;

ii. A light source and focussing system which directs a light beam (for example a laser beam) sharply focussed into the zone of analysis within the particle stream such that only a single cell will be exposed to the beam;

iii. An optical detection system, by which the scattered or fluorescent light pulses emitted by each cell at the moment when the cell passes across the beam, is collected, selected according to wavelength and converted into electronic pulses;

iv. An electronic analysis unit by which these pulses are processed and analyzed for the desired information about the cell characteristics which can be obtained from the light pulses.

A conventional optical detection system is shown schematically in FIG. 1, which is a horizontal section through a flow chamber of an FCM.

In FIG. 1, the flow chamber through which the particle stream passes is shown at 2, the section being taken at the point at which the incident light beam intersects the stream. The cell instantaneously exposed to the beam is shown at 4 and the incident light beam is shown at 6. The light pulses which are emitted from the cell 4 are collected perpendicularly to the incident beam 6 within a solid angle ($\alpha$) by a lens 8, then passed through a first beam splitter 10a. The light deflected by the first beam splitter 10a is passed through a color filter 12 onto a first photomultiplier $PM_1$ for transformation into electronic signals. The light transmitted through the first beam splitter 10a meets a second beam splitter 10b. The light respectively deflected and transmitted by the second beam splitter passes through further color filters 14, 16 to further photomultipliers, $PM_2$ and $PM_3$. Thus the light pulses are analyzed in three different parts of the wavelength spectrum.

This conventional detection system is disadvantageous in that each part of this system needs to be adjusted for correct location in three dimensions, and even with very experienced operators, initial adjustments and readjustments during measurement may involve several hours work. With systems effecting more than three color analysis, the use of a highly skilled operator is required for operation.

Further, with this conventional system, all analysis is restricted to the two dimensional plane in which the optical system is mounted. An analysis which could be carried on without such restriction would yield more information concerning the light scatter characteristics of cells, and a higher proportion of the omnidirectional, but normally weak, fluorescent light could be collected.

SUMMARY OF THE INVENTION

According to the present invention, there is provided an optical detection system in a flow cytometer, comprising an array of optical fibres which are located directly adjacent to the zone where the light from the cell is emitted, whereby the fibres act to collect emitted light.

At most, the ends of the fibres will be within a few millimeters from the cell.

BRIEF DESCRIPTION OF THE DRAWINGS

The invention will now be further described, by way of example only, with reference to the accompanying drawings, in which.

DESCRIPTION OF THE INVENTION

In accordance with the invention it has been determined that optical fibres can be used to collect directly the fluorescent or scattered light from the cell. A very simple mounting system for the fibres can be used which does not require a high accuracy in setting up. More particularly, the optical fibres may be held by the hand or fixed with a putty-like substance about 1 mm from the flow chamber and with this form of mounting the readings of scatter and fluorescence signals obtained have been found to have the same order of accuracy as achieved by a conventional optical system when set up in its optimum manner.

Figure 1:
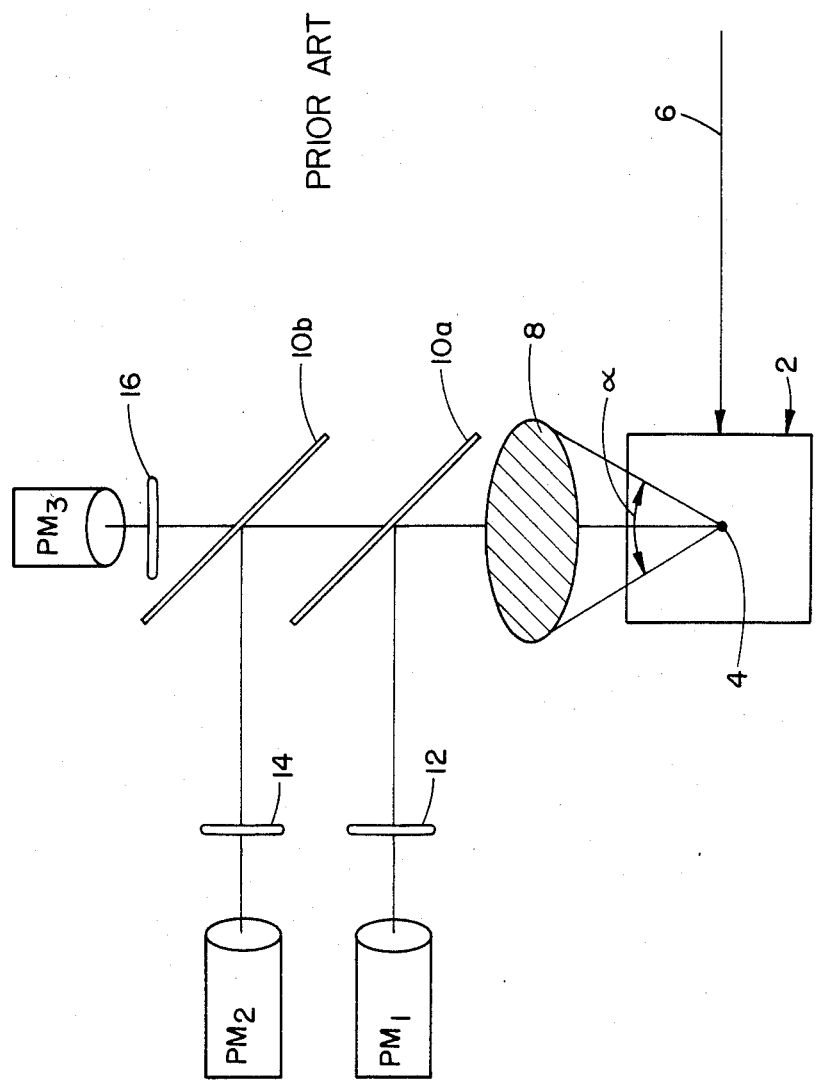
FIG. 1 is a schematic of a conventional prior art optical detection system.
Figure 2:
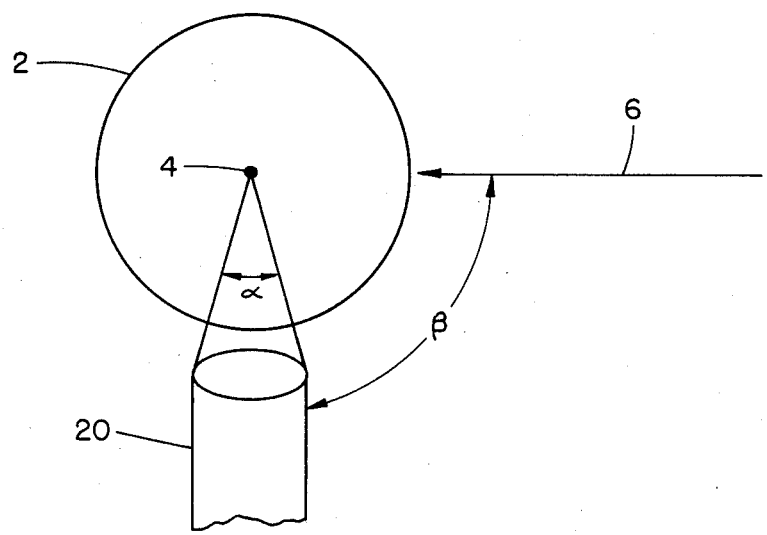
FIG. 2 is a schematic horizontal cross-section through a flow chamber of a flow cytometer to illustrate the basic principles of the present invention.

FIG. 2 shows, schematically, a horizontal section through a transparent vertical flow chamber 2 through which the particle stream passes centrally, the section being taken at the point at which the light beam intersects the stream. The excited cell is shown at 4, and the incident light beam is shown at 6. An optical fibre which directly collects the emitted light is shown at 20. In the configuration shown in FIG. 2, the optical fibre 20 collects light emitted from the cell 4 within a solid angle $\alpha$ along an axis inclined at an angle $\beta$ to the incident beam 6. As will be apparent, simply by moving the fibre 20 toward or away from the chamber 2, the measured solid angle $\alpha$ can be changed; a similar effect can be obtained by altering the size of the light-acceptance aperture by means of an aperture mask at the end of the fibre. The fibre can also be moved in order to change the angle $\beta$ relative to the incident beam 6. The choice of angles $\alpha$ and $\beta$ is not given in conventional detection systems where both angles are fixed.

Figure 3:
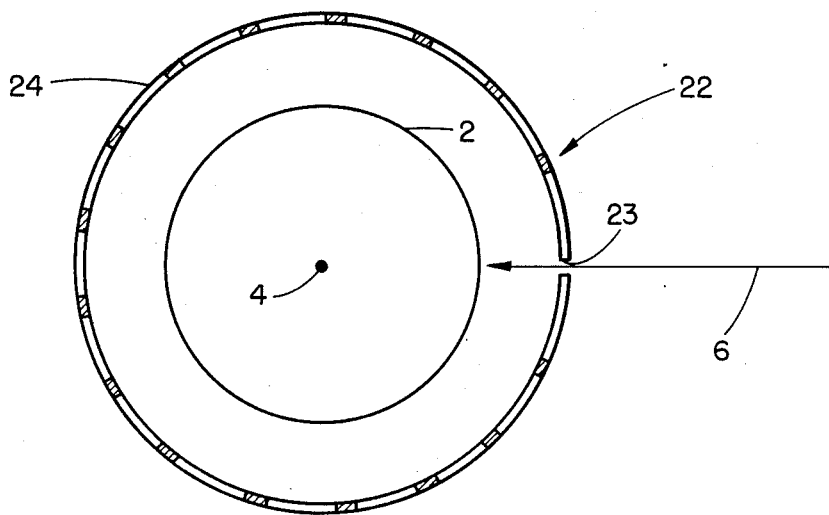
FIG. 3 is a similar horizontal section of a first practical embodiment of the invention.
Figure 4:
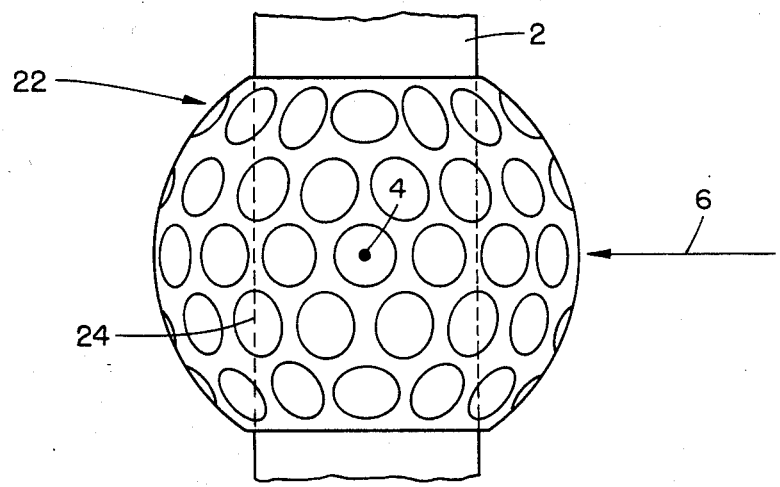
FIG. 4 is a side view of the embodiment of FIG. 3.

In one practical embodiment as shown in FIGS. 3 and 4, a part-spherical shell 22 is mounted around part of the flow chamber 2, the center of the sphere being coincident with the instantaneously excited cell 4 in the chamber 2. Thus, the center of the shell 22 is coincident with the point of intersection of the incident light beam 6 with the particle stream. The beam 6 passes through an appropriate opening 23 in the shell 22. Holes 24 are formed through the wall of the shell 22, the axis of each hole 24 lying on a different radial axis of the shell 22 so that each hole 24 faces toward the excited cell 4. A group of optical fibres is provided (not shown), the fibres leading to one or more photomultipliers. The ends of the fibres can be removably plugged into any one of the holes 24 in the shell 22 to enable readings to be taken at selected points around the cell 4, in other words at different angles of $\beta$ with the possible variation of this angle not only being in the plane of FIG. 2 but also in planes inclined to that of FIG. 2. A compromise has to be made between the desire for high angular resolution by small solid angles and the need to collect sufficient amounts of light. Therefore, in practice, the solid angle $\alpha$ of light collection for each photomultiplier also needs to be variable. Possible methods of varying the solid angle include the following:

a. Different sizes of holes 24 for fitting different diameter fibres. This would require a predetermination of angles of interest for the scatter light analysis, where the angle of resolution is important, the remaining angles being free for larger size fibres collecting the omnidirectional fluorescent light.

b. Fibre fittings for allowing variation of depth of fibre plugging, thus varying the angle of light acceptance by the distance of the light acceptance aperture from cell 4.

c. Photomultipliers for allowing collective entry of many fibres, so that for weak fluorescent light, the light from different directions may be collected by several fibres and directed into one photomultiplier.

Since fibres are relatively inexpensive, the fibres may be fixedly mounted in the shell 22. In this embodiment each hole 24 is non-removably plugged with a fibre, with the selection of light analysis angles being obtained by plugging the other ends of the relevant fibres into selected photomultipliers. This would facilitate the precision-setting of all fibres on the shell 22 and thus reduce alignment problems.

The shell 22 may be supported by a mounting system which allows adjustment of the position of the shell 22 in all directions relative to the flow chamber. Alternatively, the shell 22 may be mounted by a precision lock in a fixed position relative to the flow chamber, to thereby avoid the necessity of having to align the system subsequent to manufacture.

It is to be noted that the flow chamber 2 is not of conventional rectangular cross-section, but in the embodiment shown is of circular cross-section, the chamber being of cylindrical form. Alternatively, the chamber may be of spherical form, with the entry and exit areas of the incident light beam being flattened. In this case all non-perpendicular transitions of light through the interface between glass and air would be avoided. However, the use of a flow chamber is not essential, and the system shown in FIGS. 3 and 4 can be used in an FCM in which the particle stream moves through open air.

Figure 5:
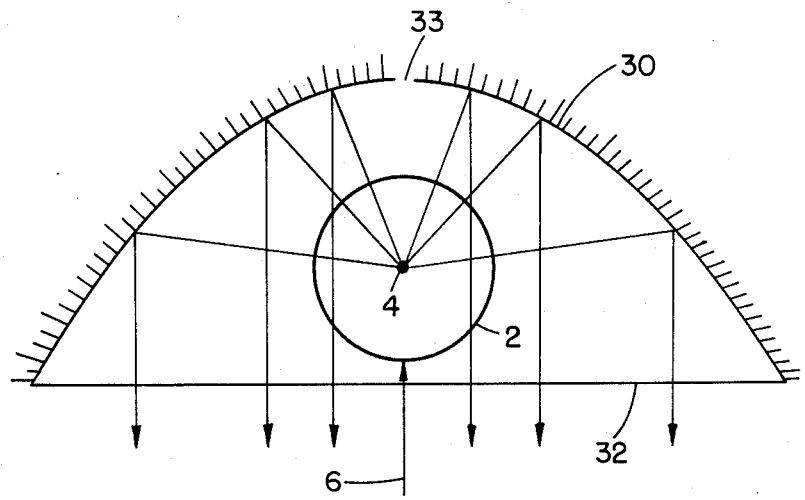
FIG. 5 is a horizontal section of a second practical embodiment of the invention.
Figure 6:
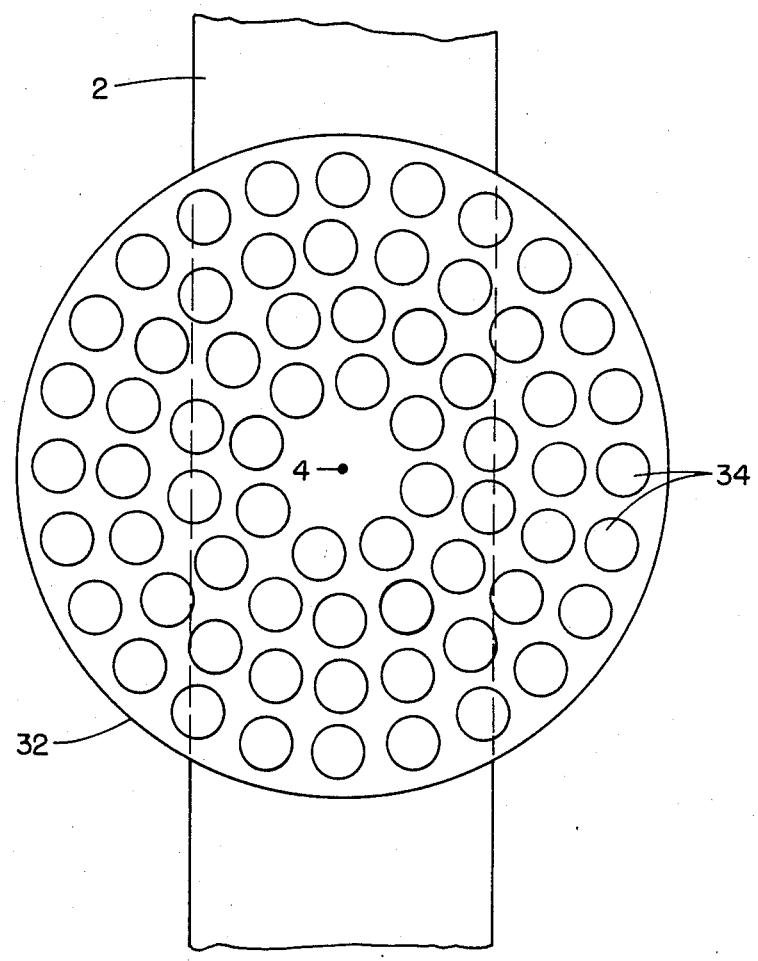
FIG. 6 is a side view of the embodiment of FIG. 5.

In another practical embodiment, as shown in FIGS. 5 and 6, the chamber 2 extends through a parabolic reflective shell 30 with the instantaneously excited cell 4 being at the focus of the parabola. This parabolic shell 30 is closed by a circular plate 32 the center of which is apertured for passage of the incident light beam 6 onto the cell 4 at the focus of the shell 30. The shell itself is provided with an aperture 33 in alignment with the central aperture in the plate to permit exit of the light beam 6. Holes 34 are formed through the plate 32 in a number of concentric rows. With each hole 34 being directed perpendicularly to the plane of the plate 32, i.e. parallel to the light beam 6.

Due to the parabolic form of the reflective shell 30, the scattered and fluorescent light will be reflected parallel to the axis of the parabola, that is at right angles to the plate 32 and parallel to the incident beam 6. Optical fibres leading to photomultipliers can be plugged into selected ones of the holes 34. As will be apparent each concentric row of holes will be associated with light scattered at the periphery of discrete cone angles, and fibres plugged into the respective rings will collect light at different points around the relevant cone angle. In effect, the use of the parabolic shell enables the collection of the light emitted all around a certain cone angle and this can be detected with high angular resolution despite an overall large area of light collection due to rings of fibres.

Instead of using a reflective paraboloid separate from the flow chamber, it might be advantageous to shape the whole flow chamber accordingly and provide the chamber with a reflective coating. This would avoid non-perpendicular transition of light through interfaces of media with different refractive indices (glass-air) and thus avoid reflection and beam-shift problems.

The use of a fixed or movable mounting system for the shell itself and of removable or non-removable fibres as discussed in connection with the previous embodiment, applies to this embodiment also.

In the two practical embodiments described, color discrimination filters can be associated with the fibres, the filters preferably being positioned at the point where the fibres enter the housing of the photomultipliers.

If light polarization studies are to be performed, polarizing filters must be applied before the light enters the fibres because of the depolarizing effect of fibre light conductors.

The use of optical fibres to directly collect the emitted light provides enhanced flexibility of measurement in relation to that of a conventional optical system, and permits easier setting up of experiments. More specifically, the main advantages of the described systems are:

i. Reduction of optical alignment problems;

ii. Reduced need for highly skilled personnel for operating the system;

iii. Reduced cost of flow cytometers;

iv. Increased versatility for sophisticated non-routine investigations on cell discrimination.

While illustrative embodiments of the subject invention have been described and illustrated, it is obvious that various changes and modifications can be made therein without departing from the spirit of the present invention which should be limited only by the scope of the appended claims.

What is claimed is:

1. A flow cytometer comprising:

a. means for transporting a stream of particles having cells in suspension in a substantially vertical particle stream, such that each cell passes singly in a vertical direction through an analysis zone;

b. a light source for directing a light beam to intersect said particle stream at said analysis zone, such that only a single cell is exposed to said light beam at one time;

c. an optical detection means for detecting scattered or fluorescent light pulses from each cell as it passes through said analysis zone, said optical detection means comprising a shell with a substantially spherical shape and having a substantially vertical passage therethrough, through which said substantially vertical particle stream is directed, and said analysis zone being located substantially centrally within said spherically shaped shell, and said shell having an array of apertures therein around said analysis zone, and a plurality of optical fibers being provided, with each optical fiber extending through an aperture in said spherically shaped shell to collect light at a particular radial axis defined by the radial position of the aperture in the shell, and wherein each optical fiber collects light within a collection angle defined by the diameter of the spherically shapted shell, the outer perimeter of the optical fiber, and the distance of the end of the optical fiber from said analysis zone, and each aperture includes means for adjustably securing the optical fiber passing therethrough to adjust the distance of the end of the optical fiber from said analysis zone, and thereby the collection angle of the optical fiber; and d. electronic means connected to said optical fibers for converting the light collected by said optical fibers into electrical impulses and analyzing said impulses for the desired information.

2. A flow cytometer as claimed in claim 1, wherein said optical fibers are removably mounted within said apertures, thereby permitting light to be collected at different incident angles.

3. A flow cytometer as claimed in claim 1, wherein a plurality of said optical fibers are connected to a common photomultiplier for allowing light from different incident and collection angles to be analyzed together.

4. A flow cytometer as claimed in claim 1, wherein said electronic means includes at least one photomultiplier.

5. A flow cytometer as claimed in claim 4, further including a color discriminating filter connected to each of said fibers.

6. A flow cytometer as claimed in claim 5, wherein each color discriminating filter is positioned between each optical fiber and a photomultiplier.

* * * * *